US005716952A

United States Patent [19]
WoldeMussie et al.

[11] Patent Number: 5,716,952
[45] Date of Patent: Feb. 10, 1998

[54] METHOD FOR REDUCING INTRAOCULAR PRESSURE IN THE MAMMALIAN EYE BY ADMINISTRATION OF MUSCARINIC ANTAGONISTS

[75] Inventors: Elizabeth WoldeMussie, Laguna Niguel; Guadalupe Ruiz, Corona, both of Calif.

[73] Assignee: Allergan, Waco, Tex.

[21] Appl. No.: 853,374

[22] Filed: Mar. 18, 1992

[51] Int. Cl.$^6$ .......... A61K 31/55; A61K 31/445; A61K 31/34; A61K 31/135

[52] U.S. Cl. .......... 514/220; 514/315; 514/468; 514/654; 514/913

[58] Field of Search .......... 514/220, 315, 514/468, 654, 913

[56] References Cited

U.S. PATENT DOCUMENTS

| | | | |
|---|---|---|---|
| 2,918,407 | 12/1959 | Biel | 167/65 |
| 3,467,756 | 9/1969 | Stone | 424/283 |
| 3,743,734 | 7/1973 | Schmidt et al. | 424/250 |
| 4,197,301 | 4/1980 | Smith et al. | 424/251 |
| 4,550,107 | 10/1985 | Engel et al. | 514/220 |
| 4,556,653 | 12/1985 | Giani et al. | 514/220 |
| 4,565,821 | 1/1986 | Chiou | 514/327 |
| 4,886,815 | 12/1989 | Schachar | 514/327 |
| 4,971,966 | 11/1990 | Engel et al. | 514/220 |
| 5,066,664 | 11/1991 | Gluchowski | 514/377 |
| 5,091,528 | 2/1992 | Gluchowski | 544/105 |

FOREIGN PATENT DOCUMENTS

| | | | |
|---|---|---|---|
| 0479524 | 4/1992 | European Pat. Off. | A61K 31/445 |
| WOA9015604 | 12/1990 | WIPO | A61K 31/44 |

OTHER PUBLICATIONS

Embase Abstract of Invest. Ophthalmol., Visual Science. (USA), 1980, Bito et al.
Chemical Abstract, 13: 108137d (1988) Hagan et al.
J.A. Pino Capote, British Journal of Anesthesia, vol. 50, No. 8 1978, p. 865.
Archives Of Pharmacology, vol. 338, No. 5, 1988, pp. 476–483, J. J. Hagan et al., 'The Relative Potencies of Colinominetics and Muscarinic Antagonists on the Rat Iris in Vivo: Effects of PH on Potency of Pirenzepine and Telenzepine'.
Current Eye Research, vol. 3, No. 8, 1984, pp. 1001–1006 P.C.M. Van Pinxteren et al. 'Acetylcholine Can Exert Two Opposite Effects on Uveal Flow in Isolated Arterially Perfused Eyes of Cats and Rabbits'.
Therapie, vol. 43, No. 3, 1988, pp. 219–228, C. Giraud et al. 'Medicaments A Potentiel Anticholinergigue'.
E.C. Hulme et al., Muscarinic Receptor Subtypes, *Annu. Rev. Pharmacol Toxicol*, (1990), 30 633–73.
W. Londong, et al., Telenzepine is at least 25 times more potent than pirenzepine—a dose response and comparative secretory study in man, *Gut*, 1987, 28, 888–895.

Dammann, et al., AF–DX 116 differentiates between prejunctional muscarine receptors located on noradrenergic and cholinergic nerves, *Archives of Pharmacology*, (1989) 339:268–271.

S. Anwar–ul, et al., The cardio–selectivity of himbacine: a muscarine receptor antagonist, *Archives of Pharmacology*, (1986).

Carlo Melchiorre, et al., Differential Blockade of Muscarinic Receptor Subtypes by Polymethylene Tetraamines. Novel Class of Selective Antagonists of Cardiac M-2 Muscarinic Receptors, *J. Med. Chem.* (1987) 30, 201–204.

Anna Minarini, et al., An improved synthesis of N,N'bis [6–o–methoxphenyl methyl hexylamino]–1,8–octanediamine (methoctramine), Chemistry & Industry 2 Oct. 1989, pp. 652–653.

Stephen B. Coan, et al., Parasympathetic Blocking Agents, II, *The Journal of Organic Chemistry*, Jun. 1955, vol. 20, pp. 774–779.

*Primary Examiner*—Zohreh Fay
*Attorney, Agent, or Firm*—Gabor L. Szekeres; Robert J. Baran; Martin A. Voet

[57] ABSTRACT

Pharmaceutical compositions and a method are disclosed for treating glaucoma and/or ocular hypertension in the mammalian eye by administering to the mammalian eye the pharmaceutical composition of the invention which contains as the active ingredient one or more muscarinic antagonist compounds. Examples of muscarinic antagonists utilized in the pharmaceutical composition and method of treatment are: 10H-thieno(3,4-b)(1,5)benzodiazepin-10-one 4,9-dihydro-3-methyl-4-((4-methyl-1-piperazinyl)acetyl) (telenzepine); 5,11-dihydro-11[4'-methyl-1'-piperazinyl)-acetyl]-6H-pyrido[2,3-b][1,4]benzodiazepin-6-one (pirenzepine); racemic 11-[[2-(Diethylamino)methyl]-1-piperidinyl]-acetyl]-5,11-dihydro-6H-pyrido[2,3-b][1,4]benzodiazepin-6-one (AF-DX 116); dextrorotatory 11-[[2-(Diethylamino)methyl]-1-piperidinyl]-acetyl]-5,11-dihydro-6H-pyrido[2,3-b][1,4] benzodiazepin-6-one (AF-DX 250); an ophthalmically acceptable salt of 4-diphenylacetoxy-1,1-dimethyl piperidine (4-DAMP); α-cyclohexyl, -α-phenyl-1-piperidinepropanol (trihexyphenidyl); cyclohexanemethanol, α-phenyl, α-[3-(1-piperidinyl)-1-propynyl (hexbutinol); 6H-pyrido[2,3-b][1,4]benzodiazepin-6-one, 11-[[4-[4-(diethylamino)butyl]-1-piperidinyl]acetyl]-5,11-dihydro (AQ-RA 741); 11-H-pyrido[2,3-b][1,4]benzodiazepine-11-carboxamide, N-[2-[2-[(dipropylamino)methyl]-1-piperidinyl]ethyl]-5-, 6-dihydro-6-oxo, monomethanesulfonate (AF-DX 384); 1,8-octanediamine, N,N'-bis[6-[[2-methoxyphenyl)methyl]amino]hexyl]-tetrahydrochloride (methoctramine) and naphto[2,3-c]furan-1(3H)-one, 4-2-(1,6-dimethyl-2-piperidinyl)ethenyl]decahydro-3-methyl-, [3S-[3 α, 3a α, 4 β[1E,2(2R*,6S*)],4a β, 8a α, 9a α]](himbacine).

8 Claims, 3 Drawing Sheets

METHOD FOR REDUCING INTRAOCULAR PRESSURE IN THE MAMMALIAN EYE BY ADMINISTRATION OF MUSCARINIC ANTAGONISTS

BACKGROUND OF THE INVENTION

1. Field of the Invention

The present invention is directed to pharmaceutical compositions, and primarily to topically applied ophthalmic compositions comprising as the active ingredient one or more muscarinic anatagonist compounds. The pharmaceutical compositions are useful for reducing intraocular pressure in animals of the mammalian species. In another aspect, the present invention is directed to administering such formulations and compositions to animals of the mammalian species (including humans) for reducing intraocular pressure in the eye.

2. Brief Description of the Prior Art

Glaucoma is an optical neuropathy associated with elevated intraocular pressures which are too high for normal function of the eye, and results in irreversible loss of visual function. It is estimated in medical science that glaucoma afflicts approximately 2 per cent of the population over the age of fourty years, and is therefore a serious health problem. Ocular hypertension, i.e. the condition of elevated intaocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma. As pertinent prior art to the present invention the following are noted.

U.S. Pat. No. 3,467,756 describes anti-glaucoma and intraocular hypotensive compositions which contain in an ophthalmic vehicle 10,11-dihydro-5-(3-methylaminoipropyl)-5,10-epoxy-11-hydroxy-5H-dibenzo [a,d]cycloheptene or related derivatives.

U.S. Pat. No. 4,197,301 describes ophthalmic compositions which contain 1-(4-amino-6,7-dimethoxy-2-quinazolinyl)-4-(2-furanylcarbonyl)piperazine, also known under the name "prazosin".

U.S. Pat. No. 4,565,821 describes a method of topically administering certain dopamine antagonists to reduce ocular hypertension and to treat glaucoma.

U.S. Pat. No. 4,886,815 describes a method for treating retinal edema by administration of dopaminergic antagonists to a patient suffering from such condition.

U.S. Pat. No. 5,066,664 describes 2-hydroxy-2-alkylphenylamino)-oxazolines and thiazolines as anti-glaucoma and vasoconstrictive agents.

U.S. Pat. No. 5,091,528 describe 6 or 7-(2-imino-2-imidazolidine)-1,4-benzoxazines as α adrenergic agents useful for treating glaucoma.

The foregoing and other anti-glaucoma and ocular hypotensive compounds and agents of the prior art do not provide such treatment or cure for glaucoma and ocular hypertension which is satisfactory in all respects. Therefore, the pharmacological and related arts continue searching for additional and better anti-glaucoma and ocular hypotensive agents.

The concept of muscarinic receptors has been known in the biological sciences for a long time. Acccording to the classical definition, muscarinic receptors of living organisms, (including mammals and particularly humans) are those biological receptor sites which are selectively activated by the natural product muscarine. Muscarinic antagonists are those compounds or substances which exhibit an inhibitory action on muscarinic receptors. A review of muscarinic agonists and antagonist as well as description of research directed to classifying muscarinic receptors into several subtypes is provided in the article titled MUSCARINIC RECEPTOR SUBTYPES, by E. C. Hulme et al., Annu. Rev. Pharmacol. Toxicol. 1990 30 633–73.

A number of naturally occurring and synthetic compounds which are active as anti-spasmodics, inhibitors of stomach juice excretion, anti-emetics, anti-secretory or cardiovascular agents, have been established to be muscarinic antagonists. In this regard the following patents are mentioned as background to the present invention.

U.S. Pat. No. 3,743,734 describes 11-aminoacetyl-5,11-dihydro-6H-pyrido[2,3-b][1,4]benzodiazepin-6-one as inhibitor of stomach ulcers, stomach juice secretion, antitussive and antiemetic.

U.S. Pat. No. 4,550,107 describes condensed diazepinones as agents for treating cardiovascular disorders.

U.S. Pat. No. 4,556,653 describes acyl derivatives of 5,11-dihydro-6H-pyrido-[2,3-b][1,4]benzodiazepine-6-one and of related compounds as antisecretory, antiulcer, antimuscarinic, and spasmolytic agents.

U.S. Pat. No. 4,971,966 describes substituted 6H-pyrido [2,3-b][1,4]benzodiazapin-6-ones as agents for treating bradycardias and bradyarrhytmias.

U.S. Pat. No. 2,918,407 describes N-lower alkyl-3-piperidyl diphenyl acetates as anti-spasmodics and agents for treating upper gastrointestinal pain and spasm.

SUMMARY OF THE INVENTION

Surprisingly it has been discovered in accordance with the present invention that muscarinic antagonists are effective as anti-glaucoma agents and as agents for reducing intraocular pressure, when such agents are applied to the mammalian eye in a pharmaceutical composition, preferably in a topical ophthalmic composition. Accordingly, the present invention relates to a method of treating glaucoma, or ocular hypertension by topically administering to the mammalian eye an ophthalmic composition which contain an effective amount of a muscarinic antagonist. Preferred examples of muscarinic antagonists suitable as the active ingredients of the ophthalmic compositions of the invention are:

10H-thieno (3,4-b) (1,5) benzodiazepin-10-one 4,9-dihydro-3-methyl-4-((4-methyl-1-piperazinyl)acetyl) (telenzepine);

5,11-dihydro-11[4'-methyl-1'-piperazinyl)-acetyl]-6H-pyrido[2,3-b][1,4]benzodiazepin-6-one (pirenzepine);

racemic 11-[[2-(Diethylamino)methyl]-1-piperidinyl]-acetyl]-5,11-dihydro-6H-pyrido[2,3-b][1,4]benzodiazepin-6-one (AF-DX 116);

dextrorotatory 11-[[2-(Diethylamino)methyl]-1-piperidinyl]-acetyl]-5,11-dihydro-6H-pyrido[2,3-b][1,4] benzodiazepin-6-one (AF-DX 250, the (+) enantiomer of AF-DX 116).

an ophthalmically acceptable salt of 4-diphenylacetoxy-1,1-dimethyl piperidine (4-DAMP);

α-cyclohexyl,-α-phenyl-1-piperidinepropanol (trihexyphenidyl);

cyclohexanemethanol, α-phenyl, α-[3-(1-piperidinyl)-1-propynyl (hexbutinol);

6H-pyrido[2,3-b][1,4]benzodiazepin-6-one, 11-[[4-[4-(diethylamino)butyl]-1-piperidinyl]acetyl]-5,11-dihydro (AQ-RA 741);

11-H-pyrido[2,3-b][1,4]benzodiazepine-11-carboxamide, N-[2-[2-[(dipropylamino)methyl]-1-piperidinyl]ethyl]-5-,6-dihydro-6-oxo, monomethanesulfonate (AF-DX 384);

1,8-octanediamine, N,N'-bis[6-[[2-methoxyphenyl)methyl]amino]hexyl]-tetrahydrochloride (methoctramine);

naphto[2,3-c]furan-1(3H)-one, 4-2-(1,6-dimethyl-2-piperidinyl)ethenyl]decahydro-3-methyl-, [3S-[3 α, 3a α, 4 β[1E,2(2R*,6S*)],4a β, 8a α, 9a α]] (himbacine)

The ophthalmic compositions of the invention contain the active ingredient in a concentration range of approximately 0.0001 to 0.1 per cent weight by volume. The composition itself includes, in addition to the active ingredient, such excipients which are per se well known in the art for preparing ophthalmic compositions, particularly ophthalmic solutions. In accordance with the method of the invention the ophthalmic compositions, preferably ophthalmic solutions are applied topically to the mammalian eye approximately 1 or 2 times daily.

DETAILED DESCRIPTION OF THE INVENTION

Figure 1:
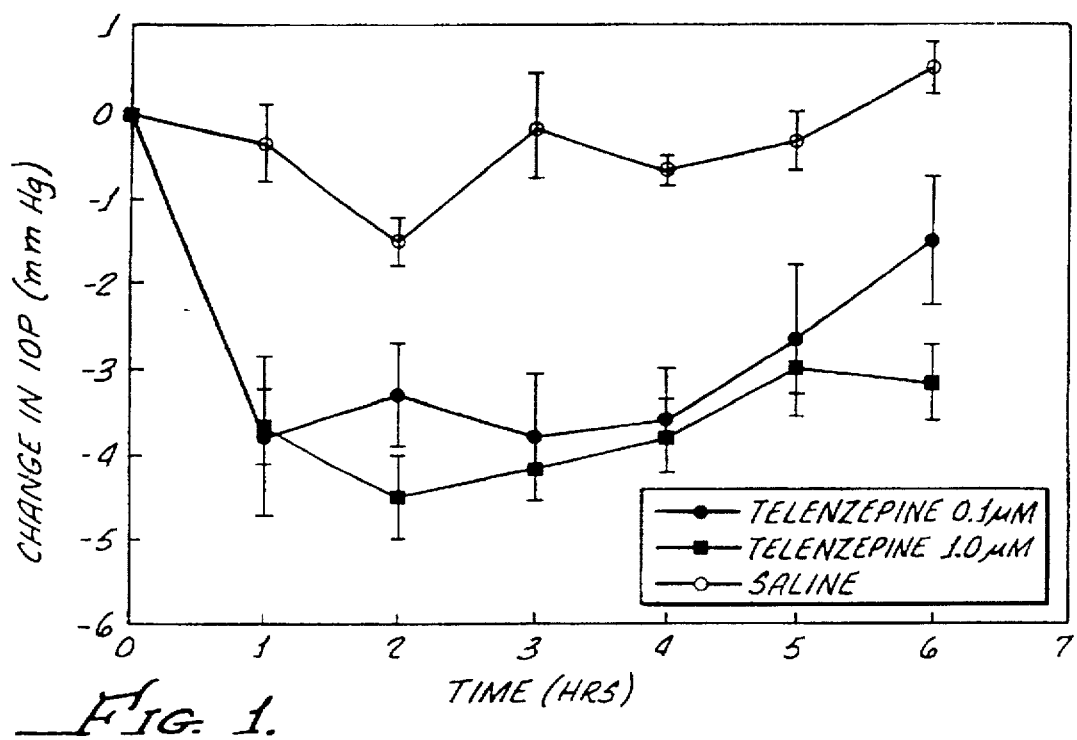
FIG. 1 is a graph showing the effect of topical administration of the drug telenzepine on the intraocular pressure (IOP) in the rabbit eye.

The compounds which are utilized in accordance with the method of the present invention, and in the pharmaceutical compositions of the present invention, are muscarinic antagonists. In this regard the term "muscarinic antagonist" is defined as in the pharmacological and related sciences where this term has a well accepted meaning. Briefly, muscarinic antagonists are those compounds which cause an inhibitory action on muscarinic receptors. Specific and preferred examples of muscarinic antagonist compounds which are utilized in accordance with the present invention are provided below.

Pharmaceutically acceptable salts of the muscarinic antagonist compounds can also be used in accordance with the present invention, where the nature of the antagonist compound permits the preparation of such salt. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide.

Preferred salts are those formed with inorganic acids such as hydrochloric acid, sulfuric acid or phosphoric acid. Any of a number of simple organic acids such as mono-, di- or tri-acid may also be used.

For reducing intraocular pressure in a mammalian eye, and particularly for treatment of glaucoma in humans suffering from that condition, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 0.1% (weight by volume) and more preferably approximately 0.0005% to approximately 0.1% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution (ocular drops).

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 0.1 |
| Preservative | 0–0.10 |
| Vehicle | 0–40 |
| Tonicity Adjustor | 1–10 |
| Buffer | 0.01–10 |
| pH Adjustor q.s. pH | 4.5–7.5 |

TABLE I-continued

| Ingredient | Amount (% W/V) |
| --- | --- |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

The ophthalmic solution (ocular drops) may be administered to the mammalian eye as often as necessary to maintain an acceptable level of intraocular pressure in the eye. In other words, the ophthalmic solution (or other formulation) which contains the muscarinic anatagonist as the active ingredient, is administered to the mammalian eye as often as necessary to maintain the beneficial hypotensive effect of the active ingredient in the eye. Those skilled in the art will recognize that the frequency of administration depends of the precise nature of the active ingredient and its concentration in the ophthalmic formulation. Within these guidelines it is contemplated that the ophthalmic formulation of the present invention will be administered to the mammalian eye approximately once or twice daily.

Examples of muscarinic antagonists which are used as the active effective ingredients in the ophthalmic compositions of the present invention are descibed and shown below:

10H-Thieno(3,4-b)(1,5)benzodiazepin-10-one 4,9-dihydro-3-methyl-4-((4-methyl-1-piperazinyl)acetyl). This compound is also known under the name telenzepine. Telenzepine may be obtained synthetically in accordance with the procedure described in U.S. Pat. No. 4,381,301. Telenzepine is also available commercially from Research Biochemicals Incorporated of Natick Mass. Ophthalmic solutions of the present invention which comprise telenzepine as the active ingredient preferably contain the drug in the concentration range of 0.0001–0.1 per cent (weight by volume). Ophthalmic preparations which contain telenzepine as the active ingredient, and the corresponding methods of treatment in accordance with the present invention, are presently most preferred.

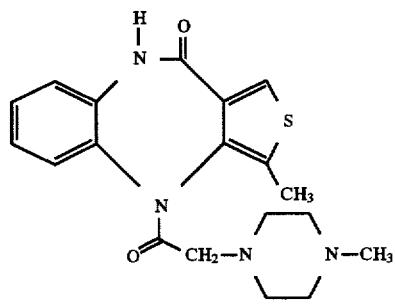

Telenzepine.

5,11-dihydro-11[4'-methyl-1-piperazinyl)-acetyl]-6H-pyrido[2,3-b][1,4]benzodiazepin-6-one is also known under the name pirenzepine. Pirenzepine can be synthesized in accordance with the procedure described in U.S. Pat. No. 3,743,734, the specification of which is incorporated herein by reference. Pirenzepine is also available commercially from Research Biochemicals Incorporated of Natick Mass. Ophthalmic preparations of the invention having pirenzepine as the active ingredient comprise approximately 0.0001 to 0.1 per cent (weight by volume) of the active ingredient.

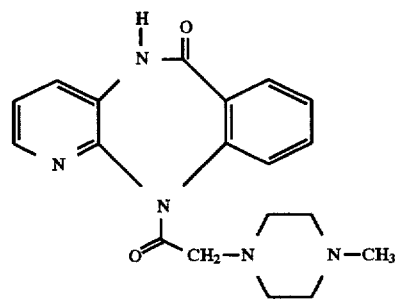

Pirenzepine

Racemic 11-[[2-(Diethylamino)methyl]-1-piperidinyl]-acetyl]-5,11-dihydro-6H-pyrido[2,3-b][1,4]benzodiazepin-6-one is also known under the designation AF-DX 116. This compound can be obtained in accordance with the procedure described in U.S. Pat. No. 4,550,107, the specification of which is incorporated herein by reference. Ophthalmic formulations of the invention comprise approximately 0.0001 to 0.1% (weight by volume) AF-DX 116.

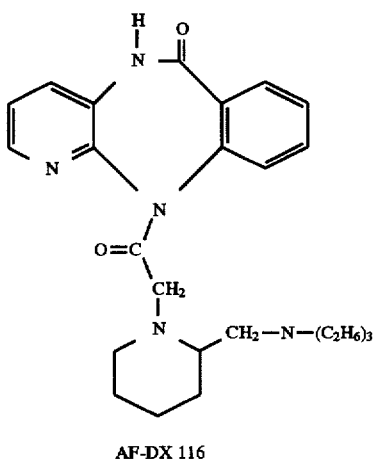

AF-DX 116

Dextrorotatory 11-[[2-(diethylamino)methyl]-1-piperidinyl]-acetyl]-5,11-dihydro-6H-pyrido[2,3-b][1,4] benzodiazepin-6-one is also known under the designation AF-DX 250. AF-DX 250 is the (+) enantiomer of AF-DX 116, the structure of which is shown above. A process for obtaining AF-DX 250 is described in *J. Med. Chem.* 32(8), 1718–24, 1989. In accordance with the invention, ophthalmic formulations comprise approximately 0.0001 to 0.1 per cent (weight by volume) of AF-DX 250 as the active ingredient.

4-Diphenylacetoxy-1,1-dimethyl piperidine bromide or iodide (or any other pharmaceutically acceptable salt of this quaternary amine) is also known in the chemical, pharmacological and related arts as 4-DAMP. This muscarinic antagonist can be obtained in accordance with the procedures described in *J. Am. Chem. Soc.* 70, 1826–1828 (1948) and *J. Or. Chem.* 20, 774–779 (1955). 4-DAMP is commercially available from Research Biochemicals Incorporated of Natick Mass. Ophthalmic formulations of the invention which include 4-DAMP comprise approximately 0.0001 to 0.1 per cent (by weight) of this active ingredient.

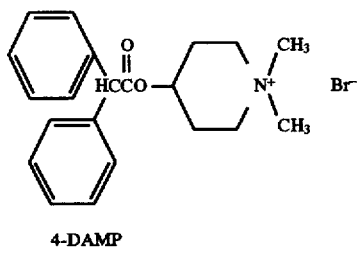

4-DAMP

α-Cyclohexyl,-α-phenyl-1-piperidinepropanol is another muscarinic antagonist which is utilized in the method and ophthalmic composition of the present invention. This compound is also known under the name trihexyphenidyl, and can be prepared in accordance with the teachings of U.S. Pat. Nos. 2,682,543 and 2,716,121, the specification of which are incorporated herein by reference. Ophthalmic compositions of the invention which include trihexyphenidyl as the active ingredient contain approximately 0.0001 to 0.1 per cent (weight by volume) of this compound.

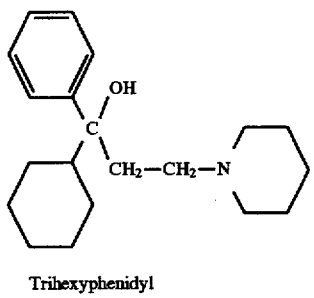

Trihexyphenidyl

Cyclohexanemethanol, α-phenyl, α-[3-(1-piperidinyl)-1-propynyl is also known under the name hexbutinol. Hexbutinol can be prepared in accordance with the teaching of (U.S. Pat. No. 2,782,191, the specification of which is incorporated herein by reference. Hexbutinol is used in a concentration range of approximately 0.0001 to 0.1 per cent (weight by volume) in the method and pharmaceutical compositions of the present invention.

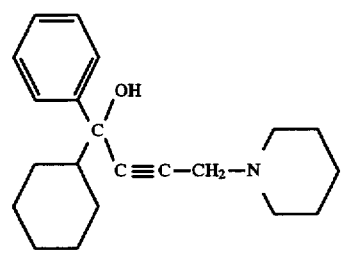

Hexbutinol

6H-Pyrido[2,3-b][1,4]benzodiazepin-6-one, 11-[[4-[4-(diethylamino)butyl]-1-piperidinyl]acetyl]-5,11-dihydro is another muscarinic antagonist which is preferred as the active ingredient in the method and pharmaceutical compositions of the present invention. This compound is also known in the relevant art under the designation AQ-RA 741, and can be prepared pursuant to the procedure described in Published European Patent Application EP312895 A2, published on Apr. 26, 1989. Pharmaceutical compositions of the invention contain this compound in the approximate concentration range of 0.0001 to 0.1 per cent.

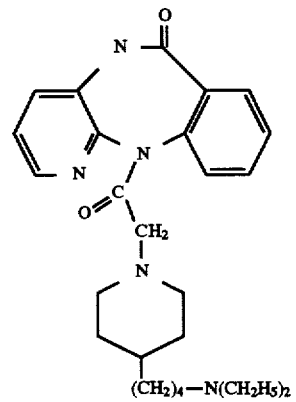

AQ-RA 741

Still another muscarinic antagonist which is preferably included as the active ingredient in the ophthalmic compositions of the present invention (and in the methods of administering the same) is 11-H-pyrido[2,3-b][1,4] benzodiazepine-11-carboxamide, N-2-[2-[(dipropylamino) methyl]-1-piperidinyl]ethyl]-5-,6-dihydro-monomethanesulfonate. This compound is also known in the relevant art under the designation AF-DX 384, and can be prepared in accordance with the teachings of U.S. Pat. No. 4,873,236, the specification of which is incorporated herein by reference. This compound is comprised in the ophthalmic compositions of the present invention in the approximate concentration range of 0.0001 to 0.1 per cent.

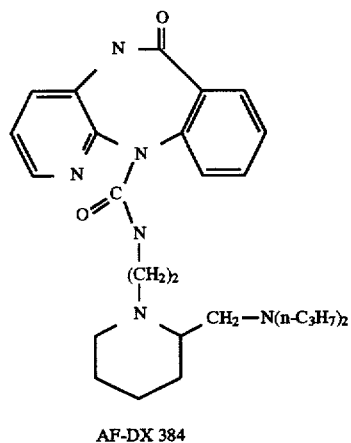

AF-DX 384

1,8-Octanediamine, N,N'-bis[6-[[2-methoxyphenyl) methyl]amino]hexyl]-tetrahydrochloride is a muscarinic antagonist which is also known under the name methoctramine. Methoctramine can be obtained in accordance with the procedure described in Chemistry and Industry (London) 89 (19) pp 652-3; and in J. Med. Chem 87 Volume 30 (1) pp 201-4. Ophthalmic compositions of the invention utilizing this active ingredient comprise approximately 0.0001 to 0.1 per cent of this compound.

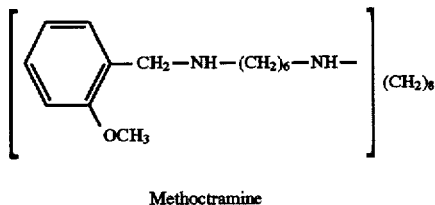

Methoctramine

Yet another example of a muscarinic antagonist which can be utilized in the method and ophthalmic compositions of the present invention, is a naturally occurring alkaloid himbacine, which is isolated from the bark of trees of the Galbulimima species, growing in Northern Queensland Australia and in Papua New Guinea. The chemical name of himbacine is naphto[2,3-c]furan-1(3H)-one, 4-2-(1,6-dimethyl-2-piperidinyl)ethenyl]decahydro-3-methyl-, [3S-[3 α, 3a α, 4 β[1E,2(2R*,6S*)],4a β, 8a α, 9a α]].

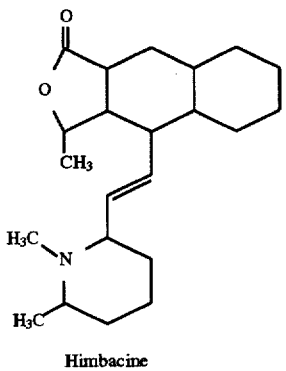

Himbacine

Himbacine is comprised in the ophthalmic copmpositions of the present invention in the approximate concentration of 0.0001 to 0.1 per cent.

The anti-glaucoma/ocular hypotensive effect, namely the effect of the muscarinic antagonists to reduce intraocular pressure, was confirmed by assay procedures conducted on New Zealand-cross Dutch belted (NZ×DB) rabbits, owl monkeys and cynomolgus monkeys.

In one assay procedure the test compounds were topically applied into one eye in normal saline solution (10 μl in owl monkeys and 25 μl in rabbits and cynomolgus monkeys. The other eye was left untreated.

In another assay procedure 20 μl of the normal saline solution of the test compounds was injected into the anterior chamber of rabbit eyes (intracameral administration). Control animals were treated with normal saline solution only.

Intraocular pressure (IOP) was measured in the assays with pneumotonometer (BIO-RAD/Digilab), and pupil diameter (PD) was measured with a ruler (OPtistick®, Allergan), every one or two hours from time zero (time of administration) to 6 hours. Results are mean ±S.E. of three or more animals.

TABLE II shows the effect of intracameral administration of certain muscarinic antagonists on the intraocular pressure (IOP) and pupil diameter (PD) in rabbit eyes. The first column of TABLE II identifies the compound tested; the second column provides the concentrations of the tested compounds in the saline solution; the third column identifies the "RESPONSE" in terms of decreased IOP (in milimeters of mercury) taken at the time of maximum effect which was usually 4 to 5 hours after topical application; and the fifth column identifies the change (if any) in pupil diameter (expressed in milimeters.).

As it can be seen from TABLE II the tested compounds were effective in reducing IOP without a significant increase in pupil diameter.

TABLE II

EFFECT OF SELECTIVE MUSCARINIC ANTAGONISTS ON IOP AND PD IN RABBITS

| COMPOUND | CONC [nM] | RESPONSE ↓IOP (mm Hg) | PD (mm) |
|---|---|---|---|
| PIRENZEPINE | 10 | 6 | — |
| | 50 | 4 | — |
| | 100 | 4 | — |
| AF-DX 116 | 10 | 5 | — |
| | 100 | 3 | — |

TABLE II-continued

EFFECT OF SELECTIVE MUSCARINIC ANTAGONISTS
ON IOP AND PD IN RABBITS

| COMPOUND | CONC [nM] | RESPONSE ↓IOP (mm Hg) | PD (mm) |
|---|---|---|---|
| 4-DAMP | 3 | 4 | ↑1.6 |
|  | 10 | 8 | ↑1.0 |
|  | 100 | 11 | ↑0.6 |
|  | 1000 | 11 | ↑1.5 |

Figure 2:
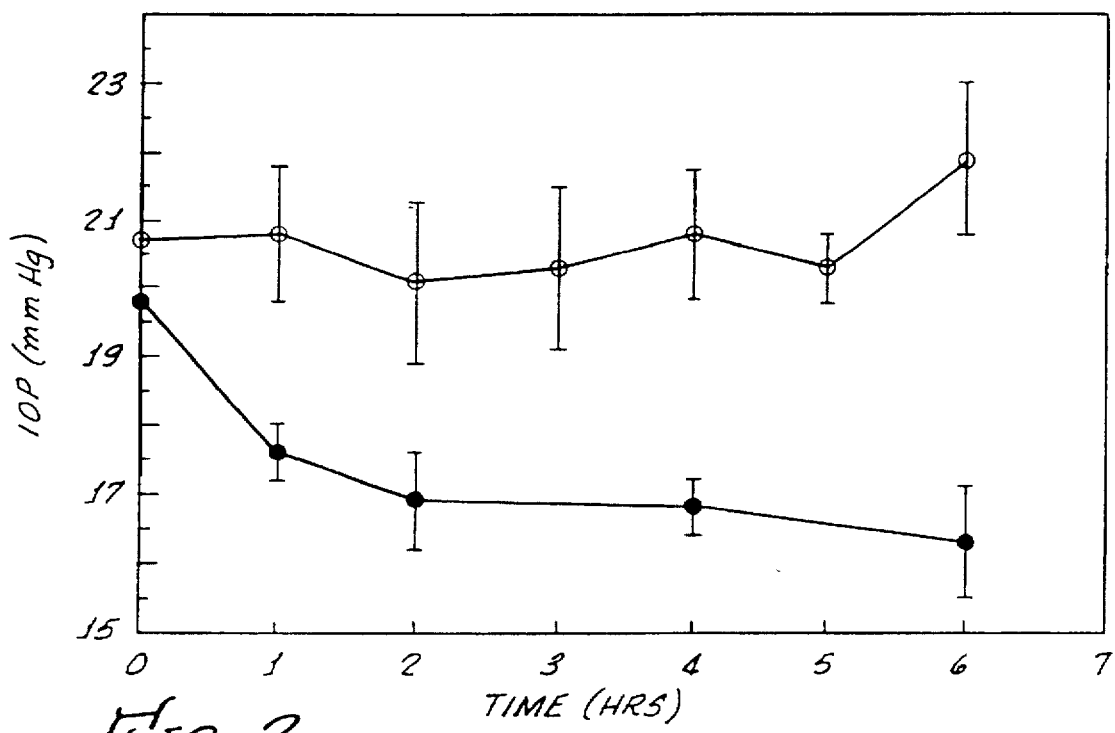
FIG. 2 is a graph showing the effect of topical administration of the drug telenzepine on the intraocular pressure (IOP) in the eye of owl monkeys.

FIGS. 1 and 2, show the effect of topical application of telenzepine (in saline solution at 0.1 micro molar, at 0.3 micro molar and at 1.0 micro molar concentrations as applicable) on the eyes of rabbits and owl monkeys, respectively. The charts of these drawing figures are self-explanatory and demonstrate the effectiveness of this muscranic antagonist as an anti-glaucoma/ocular hypotensive drug.

Figure 3:
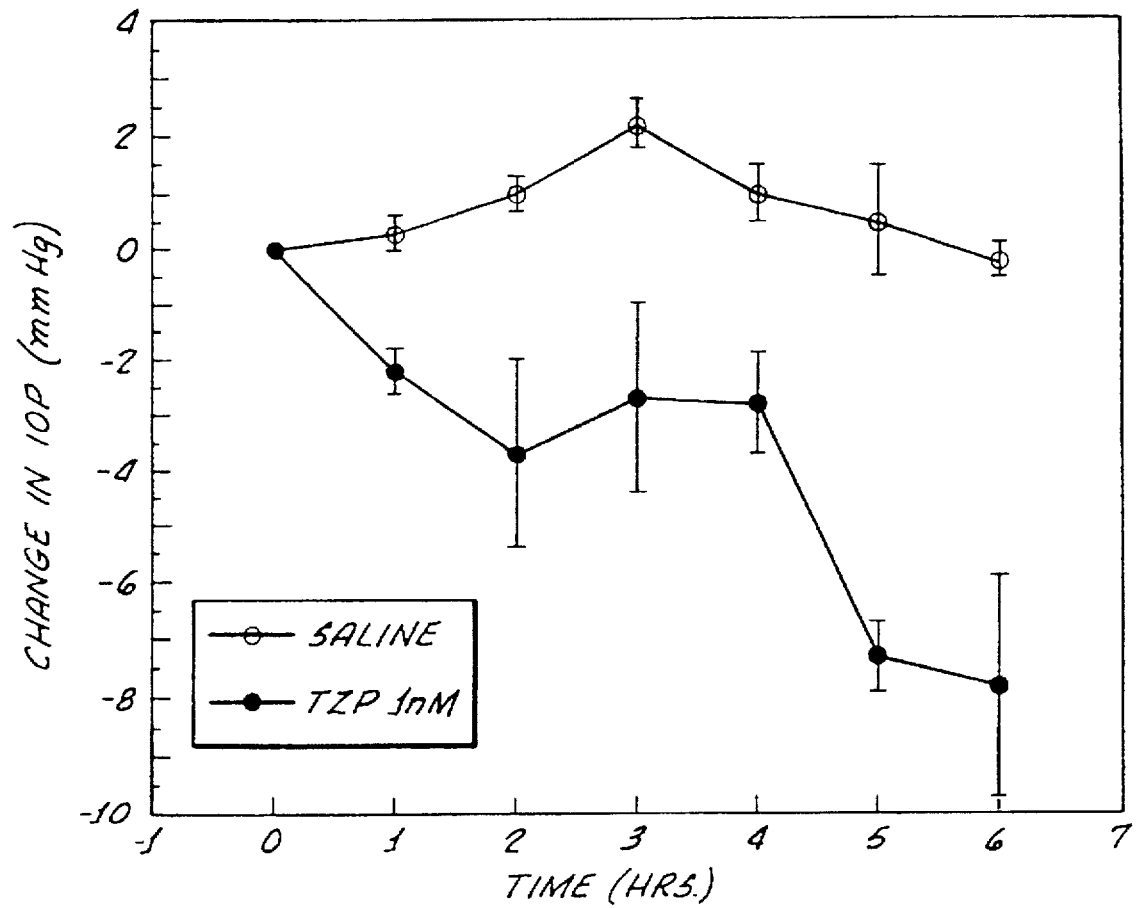
FIG. 3 is a graph showing the effect of intracameral (IC) administration of the drug telenzepine on the intraocular pressure (IOP) in the rabbit eye.

FIG. 3 demonstrates the effect of intracamerally applied telenzepine (at 1 nanomolar concentration) on the IOP in rabbits.

Figure 4:
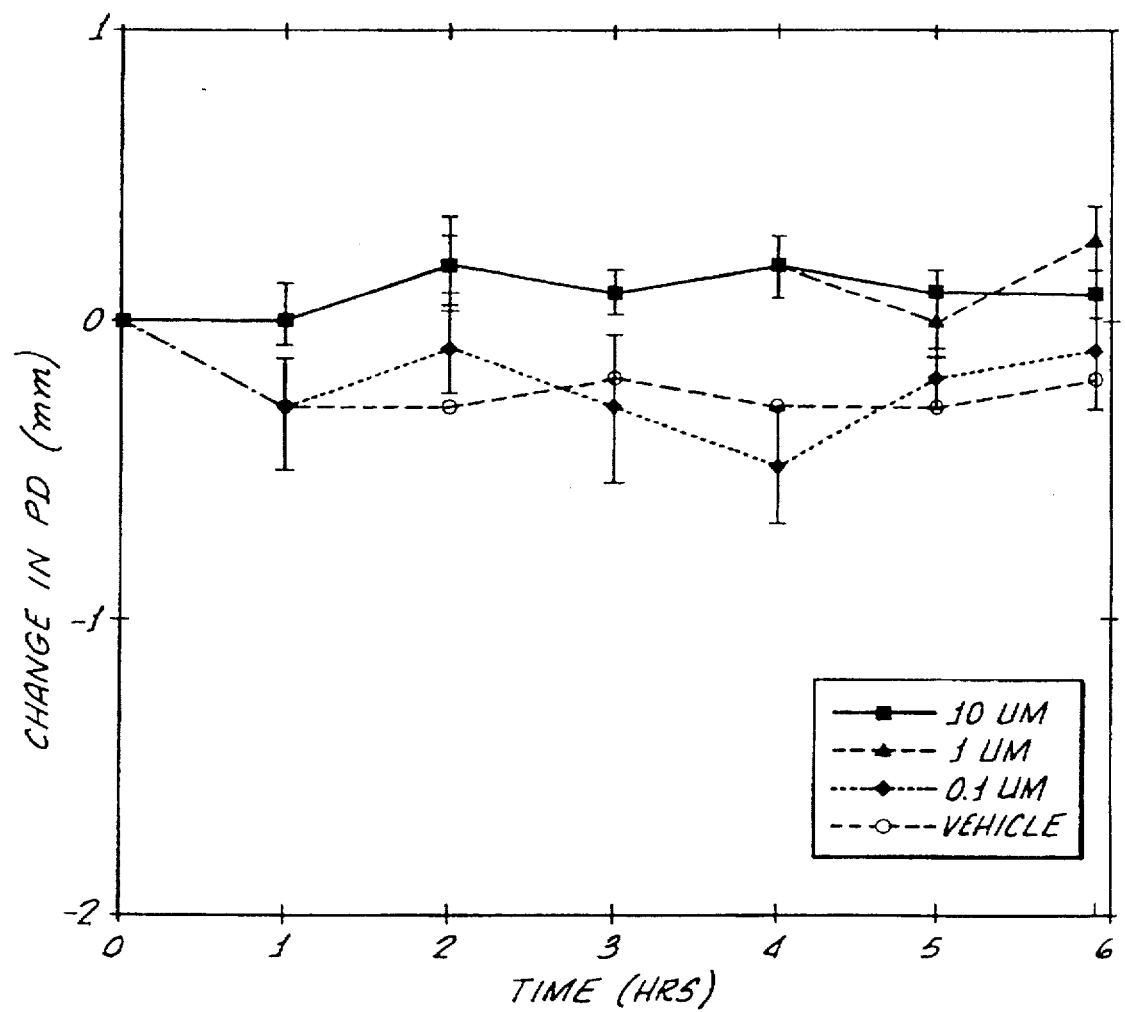
FIG. 4 is a graph showing the effect of topical administration of the drug telenzepine on the pupil diameter (PD) in the rabbit eye.

FIG. 4 demonstrates the effect of topically applied telenzepine at 0.1, 1.0 and at 10 micromolar concentrations on the pupil diameter (PD)in the rabbit eye. As it can be seen the drug does not cause an increase (or other significant change) in PD. This is a desirable feature for an anti-glaucoma/ocular hypotensive drug, as the pupil dilatory effect of some prior art anti-glaucoma drugs is considered undesirable in medical practice.

Several modifications of the present invention may become readily apparent to those skilled in the art in light of the present disclosure. Therefore, the scope of the present invention should be interpreted solely on the basis of the follwing claims, as such claims are read in light of the disclosure.

What is claimed is:

1. A method of treating animals of the mammalian species, including humans, for the purpose of reducing intraocular pressure in the eye of the mammal, the method of treatment comprising the steps of administering to the mammal a pharmaceutical composition which comprises as its active ingredient one or more muscarinic antagonist compounds, the active ingredient being present in the composition in the concentration range of 0.0001 to 0.1 per cent weight by volume.

2. The method of treatment of claim 1 where the composition is an ophthalmic solution adapted for administration to the eye of a mammal in the form of eye droplets.

3. A method of treating animals of the mammalian species, including humans, for the purpose of reducing intraocular pressure in the eye of the mammal, the method of treatment comprising the steps of administering to the mammal an ophthalmic composition which comprises as its active ingredient one or more muscarinic antagonist compounds selected from a group consisting of:

10H-thieno(3,4-b)(1,5)benzodiazepin-10-one 4,9-dihydro-3-methyl-4-((4-methyl-1-piperazinyl)acetyl) (telenzepine), 5,11-dihydro-11[4'-methyl-1'-piperazinyl)-acetyl]-6H-pyrido[2,3-b][1,4]benzodiazepin-6-one, (pirenzepine)

racemic 11-[[2-(Diethylamino)methyl]-1-piperidinyl]-acetyl]-5,11-dihydro-6H-pyrido[2,3-b][1,4]benzodiazepin-6-one (AF-DX 116), dextrorotatory 11-[[2-(Diethylamino)methyl]-1-piperidinyl]-acetyl]-5,11-dihydro-6H-pyrido[2,3-b][1,4]benzodiazepin-6-one (AF-DX 250), an ophthalmically acceptable salt of 4-diphenylacetoxy-1,1-dimethyl piperidine (4-DAMP), α-cyclohexyl,-α-phenyl-1-piperidinepropanol (trihexyphenidyl), cyclohexanemethanol, α-phenyl, α-[3-(1-piperidinyl)-1-propynyl (hexbutinol), 6H-pyrido[2,3-b][1,4]benzodiazepin-6-one, 11-[[4-[4-(diethylamino)butyl]-1-piperidinyl]acetyl]-5,11-dihydro (AQ-RA 741), 11-H-pyrido[2,3-b][1,4]benzodiazepine-11-carboxamide, N-[2-[2-[(dipropylamino)methyl]-1-piperidinyl]ethyl]-5-,6-dihydro-6-oxo, monomethanesulfonate (AF-DX 384), 1,8-octanediamine, N,N'-bis[6-[[2-methoxyphenyl)methyl]amino]hexyl]-tetrahydrochloride (methoctramine) and naphto[2,3-c]furan-1(3H)-one, 4-2-(1,6-dimethyl-2-piperidinyl)ethenyl]decahydro-3-methyl-, [3S-[3 α, 3a α, 4 β[1E,2(2R*,6S*)],4a β, 8a α, 9a α]] (himbacine), the active ingredient being present in the composition in the concentration range of 0.0001 to 0.1 per cent weight by volume.

4. The method of treatment of claim 3 where the composition is an ophthalmic solution adapted for administration to the eye of a mammal in the form of eye droplets.

5. The method of treatment of claim 3 where the muscarinic antagonist is selected from a group consisting of:

10H-thieno(3,4-b)(1,5)benzodiazepin-10-one 4,9-dihydro-3-methyl-4-((4-methyl-1-piperazinyl)acetyl) (telenzepine), 5,11-dihydro-11[4'-methyl-1'-piperazinyl)-acetyl]-6H-pyrido[2,3-b][1,4]benzodiazepin-6-one, (pirenzepine)

racemic 11-[[2-(Diethylamino)methyl]-1-piperidinyl]-acetyl]-5,11-dihydro-6H-pyrido[2,3-b][1,4]benzodiazepin-6-one (AF-DX 116), and an ophthalmically acceptable salt of 4-diphenylacetoxy-1,1-dimethyl piperidine (4-DAMP).

6. The method of treatment of claim 5 where the composition is an ophthalmic solution adapted for administration to the eye of a mammal in the form of eye droplets.

7. The method of treatment of claim 5 wherein the muscarinic antagonist is 10H-thieno(3,4 -b)(1,5) benzodiazepin-10-one 4,9-dihydro-3-methyl-4-((4-methyl-1-piperazinyl)acetyl) (telenzepine).

8. The method of treatment of claim 7 where the composition is an ophthalmic solution adapted for administration to the eye of a mammal in the form of eye droplets.

* * * * *

UNITED STATES PATENT AND TRADEMARK OFFICE
CERTIFICATE OF CORRECTION

PATENT NO. : 5,716,952  
DATED : February 10, 1998  
INVENTOR(S) : WoldeMussic et al.

Page 1 of 2

It is certified that error appears in the above-indentified patent and that said Letters Patent is hereby corrected as shown below:

Column 1, line 12, "anatagonist" should be --antagonist--.

Column 1, line 27, "intaocular" should be --intraocular--.

Column 1, line 37, "methylaminoipropyl" should be --methylaminopropyl--.

Column 1, line 52, "describe" should be --describes--.

Column 1, line 64, "Acccording" should be --According--.

Column 2, line 42, "contain" should be --contains--.

Column 5, line 44, "anatagonist" should be --antagonist--.

Column 5, line 48, "of" (2nd occurrence) should read --on--

Column 5, line 56, "descibed" should be --described--.

Column 8, line 17, "(U.S." should be --U.S.--.

Column 10, line 17, "copmpositions" should be --compositions--.

Column 10, line 46, "milimeters" should be --millimeters--.

Column 10, line 50, "milimeters" should be --millimeters--.

Column 11, lines 19-20, "muscranic" should be --muscarinic--.

UNITED STATES PATENT AND TRADEMARK OFFICE
CERTIFICATE OF CORRECTION

PATENT NO. : 5,716,952
DATED : February 10, 1998
INVENTOR(S) : WoldeMussic et al.

It is certified that error appears in the above-indentified patent and that said Letters Patent is hereby corrected as shown below:

Column 3, line 14, "ophthalmic." should be --ophthalmic--.

Column 4, line 66, after "pH Adjustor", "q.s. pH" should be in the next column.

Signed and Sealed this

Twenty-ninth Day of December, 1998

Attest:

BRUCE LEHMAN

*Attesting Officer*

*Commissioner of Patents and Trademarks*